United States Patent [19]

America

[11] Patent Number: 4,969,938
[45] Date of Patent: Nov. 13, 1990

[54] FLUID CONNECTOR FOR MICRODEVICES

[75] Inventor: William G. America, Bethel, Conn.

[73] Assignee: The Perkin-Elmer Corporation, Norwalk, Conn.

[21] Appl. No.: 460,447

[22] Filed: Jan. 3, 1990

[51] Int. Cl.⁵ ............................................. B01D 15/08
[52] U.S. Cl. ........................................ 55/386; 55/67; 55/197
[58] Field of Search ................... 55/67, 197, 208, 386; 210/198.2, 198.3

[56] References Cited

U.S. PATENT DOCUMENTS

| Re. 31,974 | 8/1985  | Brownlee        | 55/386 X |
|------------|---------|-----------------|----------|
| 3,498,027  | 3/1970  | Buchtel, Jr.    | 55/197   |
| 4,036,803  | 5/1977  | Abrahams et al. | 55/386 X |
| 4,083,702  | 4/1978  | Hartigan et al. | 55/386 X |
| 4,422,860  | 12/1983 | Feinstein       | 55/197 X |
| 4,669,756  | 6/1987  | Cassaday et al. | 55/386 X |
| 4,690,437  | 9/1987  | Anderson, Jr.   | 55/386 X |
| 4,734,107  | 3/1988  | Trestianu et al.| 55/197 X |
| 4,787,656  | 11/1988 | Ryder           | 55/386 X |
| 4,792,396  | 12/1988 | Gundelfinger    | 55/386 X |
| 4,818,264  | 4/1989  | Langhorst       | 55/386 X |

Primary Examiner—Robert Spitzer
Attorney, Agent, or Firm—H. S. Ingham; E. T. Grimes

[57] ABSTRACT

A microdevice assembly includes a miniature fluid processing device of silicon with a fluid orifice therein. A high-silica glass attachment member sealed to the device has an aperture with a narrow portion aligned with the orifice and a conical portion with a conical wall diverging from the narrow portion. A tube with a soft graphite ferrule thereon is inserted into the conical portion. A rigid package member includes a base supporting the device, a cover disposed proximate the attachment member, and side walls connecting the base and the cover. A threaded opening through the cover is aligned with the aperture. An externally threaded nut with a hole therethrough is fitted slidingly over the tube, and is tightened into the threaded opening so as to sealingly compress the ferrule between the wall and the tube.

7 Claims, 1 Drawing Sheet

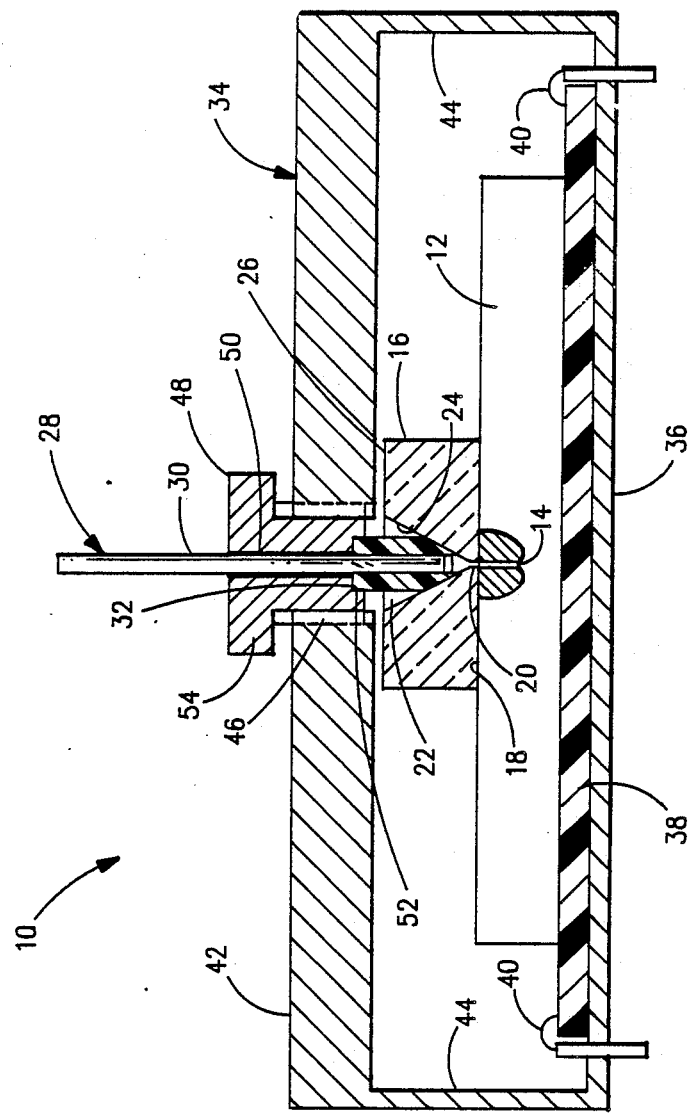

4,969,938

FLUID CONNECTOR FOR MICRODEVICES

The present invention relates to miniature fluid devices and particularly to connections for fluid flow to such devices.

BACKGROUND OF THE INVENTION

Miniature devices for control or analysis of fluids formed of silicon or the like, also known as microdevices, have been produced using the techniques of integrated electronic circuit chip processing. Such devices, for example, are utilized for gas chromatography as taught in copending U.S. patent application Ser. No. 330,246 filed Mar. 29, 1989, (Goedert) of the present assignee. A device receives fluids, typically a carrier gas and an injected sample, for valving, analysis or other processing in the microdevice.

A problem is making a fluid-flow connection for the device to receive and/or exit the fluid. Currently connections are made by bonding small tubes directly to the devices, a technique that is tricky and does not allow for easy interchanging of components. Since miniature fluid devices are particularly useful in extreme ranges of temperatures, a particular requirement is withstanding moderate high temperatures such as 400° C. Also, in such devices designed for gas chromatography, chemical resistance against corrosive sample compounds is needed. Ordinary bonding with polymer cement is not satisfactory for such conditions. Polymers, including epoxies and polyimides lose mechanical strength as temperature increases. Polymers readily oxidize in air and also decrease in strength with time.

Connectors for ordinary size fixtures are well know, such as structures incorporating elastomer o-rings and brass ferrule shells that are slid over tubes. However miniature fluid devices have particular problems as indicated above, not solved by conventional connecting structures.

Therefore an object of the invention is to provide a novel fluid microdevice assembly with a fluid connection to a miniature fluid processing device. Other objects are to provide such an assembly with an easily interchangeable fluid connection, elevated temperature capability, and chemical corrosion resistance.

SUMMARY OF THE INVENTION

The foregoing and other objects are achieved in a fluid microdevice assembly including a miniature fluid processing device having an attachment surface with an orifice therein receptive of fluid. An attachment member is sealed to the attachment surface and has an aperture therethrough. The aperture has a narrow portion aligned with the orifice in fluid communication therewith, and further has a conical portion with a conical wall diverging from the narrow portion toward an outer surface of the attachment member.

The microdevice assembly further includes a tube subassembly comprising a tube and a ferrule fitted snugly over the tube, the ferrule being formed of a ductile material, preferably soft graphite. The subassembly is inserted into the conical portion of the aperture with the ferrule contacting the conical wall. A rigid package member substantially encloses the device and the attachment member, and comprises a base for supporting the device, a cover disposed proximate the outer surface of the attachment member, and support means for connecting the base and the cover. The cover has a threaded opening therethrough aligned with the aperture. An externally threaded nut with a hole therethrough smaller in diameter than the ferrule is fitted slidingly over the tube. The nut is tightened into the threaded opening so as to sealingly compress the ferrule between the conical wall and the tube. The tube is accessible externally for fluid connection.

BRIEF DESCRIPTION OF THE DRAWINGS

The drawing is an elevation, partially in section, of a fluid microdevice assembly according to the invention.

DETAILED DESCRIPTION OF THE INVENTION

With reference to the drawing a fluid microdevice assembly 10 includes a miniature fluid processing device 12 such as a gas chromatographic device of the type disclosed in the aforementioned Goedert patent application. Such a device may contain a chromatographic column, a detector, an injector and control valves, and also may have electrical control circuits therein. (For clarity of the present invention these details are not shown in the drawing.) The device has a fluid inlet orifice 14 receptive of fluid for the device. The orifice alternatively may be for fluid exit. Also, there may be several fluid connections according to the invention; only one is shown.

The device advantageously is formed at least partially of silicon or the like but may include other structural materials such as high-silica glass. An attachment member 16 is preferably formed of quartz or a high-silica glass such as Pyrex (TM) or other convenient material with a thermal expansion coefficient similar to that of the silicon. This member is sealed by bonding to an attachment surface 18 of the silicon device 12. Anodic bonding of the glass to the silicon may be effected by heating them together under a small compressive load to 350° C. for 10 minutes with a DC voltage of 1500 V.

The attachment member 16 has an aperture therethrough, with a narrow portion 20 aligned with the orifice 14 in the device in fluid communication therewith. The aperture further has a conical portion 22 with a conical wall 24 diverging from the narrow portion 20 toward an outer surface 26 of the attachment member. A further cylindrical portion may extent from the conical portion to the surface, but this is not necessary (and is not shown).

A tube subassembly 28 is made up of a tube 30 and a cylindrical ferrule 32 fitted snugly over the tube, the ferrule being formed of a ductile material, preferably a soft graphite for withstanding elevated temperatures and corrosive environments. For the same reasons the tube is advantageously formed of high-silica glass. The subassembly is inserted into the conical portion 22 of the aperture with the ferrule 32 contacting the conical wall 24.

A rigid package member 34 partially or completely encloses the device and the attachment member. The package is basically standard, such as an integrated circuit dual in-line package, modified as necessary to incorporate features described herein. The package has a base 36 for supporting the device. A ceramic substrate 38 with gold pattern electrical contacts (not shown) may be interposed on the base in contact with corresponding patterns under the device 12, and electrical connections 40 may be passed through the base 36 as needed for operating the device. The member 34 includes a cover 42 disposed proximate the top 26 of the attachment member. Support means, generally constituting side walls 44 of the package 34, connect the base 36 and the cover 42.

The cover 42 has a threaded opening 46 therethrough aligned with the aperture, and should be sufficiently thick to accommodate several turns of the threading. An externally threaded nut 48 has a hole 50 therethrough smaller in diameter than the ferrule 32, and sized so as to loosely fit over the tube 30. The nut should have a central recess 52 to retain the ferrule. The nut has a suitably shaped upper portion 54 for engagement with a wrench, and is engaged and tightened into the threaded opening 46 so as to sealingly compress the ferrule 32 between the conical wall 24 and the tube 30. The lower end of the ductile ferrule should deform to seal against the conical wall. The tube 30 extends from the nut 48 so as to be accessible externally for fluid connection.

As an example the silicon device is 0.5 mm thick by 1.4 cm × 1.8 cm, and the attachment member is 6.4 mm diameter by 4.8 mm long. The internal cone 24 is 2.5 mm diameter at its widest opening and has an included angle of 40°. The narrow portion 20 of the aperture is 0.45 mm diameter. The tube 30 has an outside diameter of 0.8 mm and the ferrule 32 is 2.0 mm diameter and 3.0 mm long and the recess 52 into the nut is 1.0 mm. A small gap 56 such as 0.5 mm between the cover 42 and the attachment member 16 allows for thermal expansion without the cover contacting the member. This assembly 10 is capable of creating a leak-free fluid seal of 14 kg/cm$^2$ (200 psi) at 400° C. with helium.

While the invention has been described above in detail with reference to specific embodiments, various changes and modifications which fall within the spirit of the invention and scope of the appended claims will become apparent to those skilled in this art. Therefore, the invention is intended only to be limited by the appended claims or their equivalents.

What is claimed is:

1. A fluid microdevice assembly comprising:
   a miniature fluid processing device having an attachment surface with an orifice therein receptive of fluid;
   an attachment member sealed to the attachment surface and having an aperture therethrough, the aperture having a narrow portion aligned with the orifice in fluid communication therewith and a conical portion with a conical wall diverging from the narrow portion toward an outer surface of the attachment member;
   a tube subassembly comprising a tube and a ferrule fitted snugly over the tube, the ferrule being formed of ductile material, and the subassembly being inserted into the conical portion of the aperture with the ferrule contacting the conical wall;
   a rigid package member substantially enclosing the device and the attachment member, comprising a base for supporting the device, a cover disposed proximate the outer surface of the attachment member, and support means for connecting the base and the cover, the cover having a threaded opening therethrough aligned with the aperture; and
   an externally threaded nut with a hole therethrough smaller in diameter than the ferrule and fitted slidingly over the tube, the nut being tightened into the threaded opening so as to sealingly compress the ferrule between the conical wall and the tube, and the tube being accessible externally for fluid connection.

2. The assembly according to claim 1 wherein the ferrule is formed of soft graphite.

3. The assembly according to claim 1 wherein the device is formed at least partially of silicon and the attachment member is formed of quartz or a high-silica glass bonded to the silicon.

4. The assembly according to claim 1 wherein the tube is formed of high-silica glass.

5. The assembly according to claim 1 wherein the ferrule is formed of soft graphite, the device is formed at least partially of silicon, and the attachment member is formed of quartz or a high-silica glass bonded to the silicon.

6. The assembly according to claim 1 wherein the nut has a central recess to retain the ferrule.

7. The assembly according to claim 1 wherein the fluid processing device is a gas chromatography device.

* * * * *